United States Patent [19]

Thorsson et al.

[11] 4,358,536
[45] Nov. 9, 1982

[54] PRODUCTION OF ETHANOL

[75] Inventors: Conny R. Thorsson, Jarfalla; Indrek J. Viira, Danderyd, both of Sweden

[73] Assignee: Alfa-Laval AB, Tumba, Sweden

[21] Appl. No.: 123,716

[22] Filed: Feb. 22, 1980

[30] Foreign Application Priority Data

Feb. 27, 1979 [SE] Sweden ............................... 7901738

[51] Int. Cl.³ .................... B01D 3/16; C07C 29/80; C12P 7/06
[52] U.S. Cl. ................................... 435/161; 202/153; 202/174; 203/19; 203/25; 203/26; 203/47; 203/74; 203/75; 203/76; 203/82; 203/83; 203/84; 203/85; 203/DIG. 13; 426/11; 426/494
[58] Field of Search ............... 435/161, 162, 163–165; 159/47 R, 24 A, 17 R; 426/11, 14, 494, 493, 11; 203/19, 87, 22, 25, 47, 27, 95, DIG. 13, 71–85; 202/174, 153

[56] References Cited

U.S. PATENT DOCUMENTS

| | | | |
|---|---|---|---|
| 504,074 | 8/1893 | Bradley | 435/165 |
| 1,912,010 | 5/1933 | Ricardi et al. | 203/85 |
| 2,010,929 | 8/1935 | Reich | 203/27 |
| 2,127,138 | 8/1938 | Reich | 203/27 |
| 2,152,164 | 3/1939 | Wentworth | 203/27 |
| 2,155,134 | 4/1939 | Karsch | 435/162 |
| 2,358,272 | 9/1944 | Willkie | 426/494 |
| 2,372,854 | 4/1945 | Reich | 435/162 |
| 2,440,925 | 5/1948 | Boeckeler | 435/462 X |
| 2,698,826 | 1/1955 | Peltzer | 435/161 |
| 2,892,757 | 6/1959 | Markham | 203/28 |
| 3,884,770 | 5/1975 | Misselhorn | 203/85 |

Primary Examiner—Wilbur L. Bascomb, Jr.
Attorney, Agent, or Firm—Davis, Hoxie, Faithfull & Hapgood

[57] ABSTRACT

A flow of fermenting liquor from a fermentor is separated into a yeast concentrate flow, which is recirculated to the fermentor, and a yeast-free flow which is separated in a simple evaporator unit into a first ethanol-enriched vapor flow and a first liquid bottom flow. The first vapor flow is treated to produce the desired ethanol while a major part of the first liquid bottom flow is recirculated to the fermentor. A minor, residual part of the latter flow is fed to a stripping unit where it is separated into a second ethanol-enriched vapor flow and a second liquid bottom flow exhausted of ethanol.

14 Claims, 8 Drawing Figures

PRODUCTION OF ETHANOL

THE DISCLOSURE

This invention relates to a method for producing ethanol by fermentation of a substrate containing carbohydrate in one or a number of fermentors, a flow of fermenting liquor being separated for instance by centrifugal separation into at least one yeast concentrate flow and one yeast-free flow, the yeast concentrate flow being recirculated to the fermentor while the yeast-free flow is separated by distillation into one flow enriched in ethanol and one residual flow, part of which is recirculated to the fermentor.

Such a method is disclosed in Swedish Patent Specification No. 7801133-5. When separating the yeast-free flow by distillation, the bottom flow discharged from the plant is called "slop". It is essential that this slop be concentrated in a dissolved, solid substance, primarily of a non-fermentable nature, in order that it can be disposed of in an economical way, as by drying or burning. The slop is more utilizable as a fertilizer in farming at a high concentration, as the costs for transportation will be lower. In order to achieve good operational economy when producing ethanol, simultaneously obtaining slop, a considerable fraction of said residual flow must be recirculated to the fermentor, and the yeast-free flow which is separated by distillation must contain a relatively high content of dissolved, solid substance, primarily of a non-fermentable nature. In this way some problems arise, however. A high concentration of dissolved, solid substance in the flow which is fed to a distillation plant may result in the formation of deposits, especially in those parts of this plant which are close to the feed point. A large part of recirculated residual flow also means that the flow from which the ethanol is to be obtained is correspondingly large, so that the equipment must be dimensioned accordingly with corresponding high investment costs.

The principal object of this invention is to avoid these drawbacks in a method of the aforementioned type which is operated in such a way that the content of solid substance in said residual flow is relatively high. This is achieved by feeding the yeast-free flow to a simple evaporator unit, corresponding to one or only a few distilling stages, wherein it is separated into (1) a first vapor flow, enriched in ethanol, which is fed to a plant for the production of the desired ethanol quality, and (2) a first liquid bottom flow, of which a major part is recirculated to the fermentor while a minor, residual part is fed to a stripping unit. In the latter, this minor part of the first liquid bottom flow is separated into (a) a second vapor flow enriched in ethanol and (b) a second liquid bottom flow free of ethanol. Said first liquid bottom flow corresponds to said residual flow.

By using the new method, only a small, simple evaporator unit of the distillation plant is exposed to the deposit-forming flow. This evaporator unit can be doubled without too large an investment cost, in order that no stopping of the operation is needed for the maintenance of the evaporator unit (i.e., the removal of any deposits).

As a substantial part of the incoming yeast-free flow is recirculated to the fermentor in the form of a first, liquid bottom flow after just one passage through the evaporator unit, but before reaching the stripping unit, the latter can be designed for a substantially smaller flow than would have been the case if the total yeast-free flow had been separated into one vapor flow enriched in ethanol and one final slop flow, free of ethanol, in one single stripping unit. By using a simple evaporator unit and a stripping unit, there is provided a slop with relatively high concentration without the need of a corresponding high concentration of dry solids in the fermenting liquor.

The difference in dry solids concentration between the fermenting liquor and the slop may be varied by feeding heat energy to the stripping unit accordingly, and feeding the second vapor flow enriched in ethanol to the simple evaporator unit as direct steam. It is important that this difference be maximal, as the dry solids to a large extent comprise components, which increase the osmotic pressure, which in turn influences the growing and action power of the yeast microbes extensively.

In principle, both the first and the second vapor flows enriched in ethanol are fed to a plant for the production of the desired ethanol quality. This can be performed in a variety of different ways. It must be observed that the major part of the ethanol quantity is, of course, to be found in said first vapor flow, while the second vapor flow contains certain amounts of ethanol but shows, above all, a high enthalpy. The ways of feeding said two vapor flows enriched in ethanol to a plant for the production of ethanol depend especially on the method chosen for the feeding of the energy needed for the separation in question; that is, where this energy is fed and in which form, i.e., indirectly by heat exchange from a suitable heating medium like steam or hot liquid, or directly in the form of steam. The use of direct steam has the advantage that the problem with deposit formation on the heat transfer surfaces is avoided.

According to one embodiment of the invention, the second vapor flow enriched in ethanol is fed to the simple evaporator unit. This mode of operation will mean a simple design. Alternatively, at least part of the second vapor flow enriched in ethanol can be fed directly or indirectly to the simple evaporator unit.

According to a further embodiment of the new method, at least part of the second vapor flow enriched in ethanol is combined with the first vapor flow enriched in ethanol, the combined vapor flow being fed to the plant for production of the desired ethanol quality. This feeding can be performed in different ways, as by direct feeding in vapor form into a rectifying column or, after condensing, by heat exchange against some flow. It may be suitable to use at least part of the available enthalpy in the first and second vapor flows enriched in ethanol for bottom heating of a rectifying column, from which there is discharged a concentrated ethanol flow. It is also possible to use at least part of the second vapor flow enriched in ethanol as heating medium in a rectifying column. The heating of such a rectifying column can also be performed by a so-called thermo compressor in which the heat content of some of said vapors is utilized. Even the heating of the simple evaporator unit can be performed, at least partly, by a thermo compressor.

According to another embodiment of the new method, the first vapor flow enriched in ethanol is fed to the lowest stage in a rectifying column for production of the desired ethanol quality. The liquid flow from this stage is recirculated to the evaporator unit, whereby an appreciable energy gain is obtained.

The stripping unit can be designed as a simple unit provided with only a few distilling stages, but preferably it is designed as a stripping column with distillation stages enough for making it possible to discharge from its bottom a flow which is said second liquid bottom flow containing a low content of ethanol, of the order below 0.5% (weight).

When it is aimed at achieving a maximal difference in dry solids concentration between the fermenting liquor and the slop, energy is fed indirectly to the stripping unit. If the vapor flow in the stripping unit is about the same as the vapor flow in the simple evaporator unit, the difference in dry solids concentration is of major interest. To achieve a larger difference in the ethanol concentration of liquid flows fed to and discharged from the simple evaporator unit, the number of distilling stages can be increased somewhat, in order to decrease the flows between the fermentor and the simple evaporator unit, which would reduce the apparatus load in these flows. Thus the aim would, per se, not be to remove the ethanol extensively. In a case like this it would be possible to combine the simple evaporator unit and the stripping unit to one column unit. In such case, the liquid flow returned to the fermentor would have to be discharged at a suitable level in the column.

Alternatively, the stripping unit can comprise a series of evaporator stages, the vapor flow from such an evaporator stage (n+1) being fed to the previous evaporator stage (n), the bottom flow from which it has received. Such an embodiment can be advantageous if there are severe deposit formation problems, as in this case a minor part of the stripping unit can be replaced instead of the whole of it.

Usually it is suitable to operate the simple evaporator unit and the stripping unit at a pressure close to atmospheric pressure, but in certain cases it may be advantageous to operate these units at a somewhat reduced pressure, because the temperature is thus lowered in them, which may be advantageous in reducing the formation of deposits.

The invention will now be disclosed more in detail, reference being made to the accompanying drawings, in which.

Figure 1:
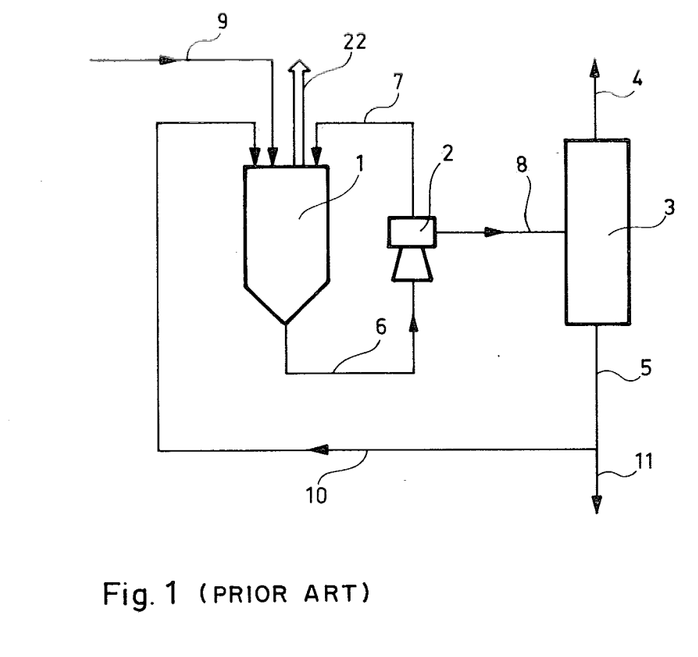
FIG. 1 is a schematic flowsheet for the method according to Swedish Patent Application No. 7801133-5.

The system shown in FIG. 1 comprises a fermentor 1, a centrifugal separator 2 for the recirculation of yeast to the fermentor, and a plant 3 for the separation of a yeast-free flow into one flow, enriched in ethanol, and a residual flow which is exhausted of ethanol but which contains a certain amount of fermentable material. The ethanol flow is discharged through a line 4 and the residual flow through a line 5. The yeast recirculation is performed through two lines 6 and 7, and the yeast-free flow is fed to plant 3 through a line 8. The raw material flow is fed to the fermentor through a line 9. Evolving $CO_2$ is discharged through a line 22.

The residual flow discharged from the plant at 5 is separated into two part-flows, one of which is recirculated to the fermentor through a line 10, whereas the second is discharged from the plant as slop through a line 11. The operation of such a plant is disclosed in said Swedish Patent Specification No. 7801133-5.

Figure 2:
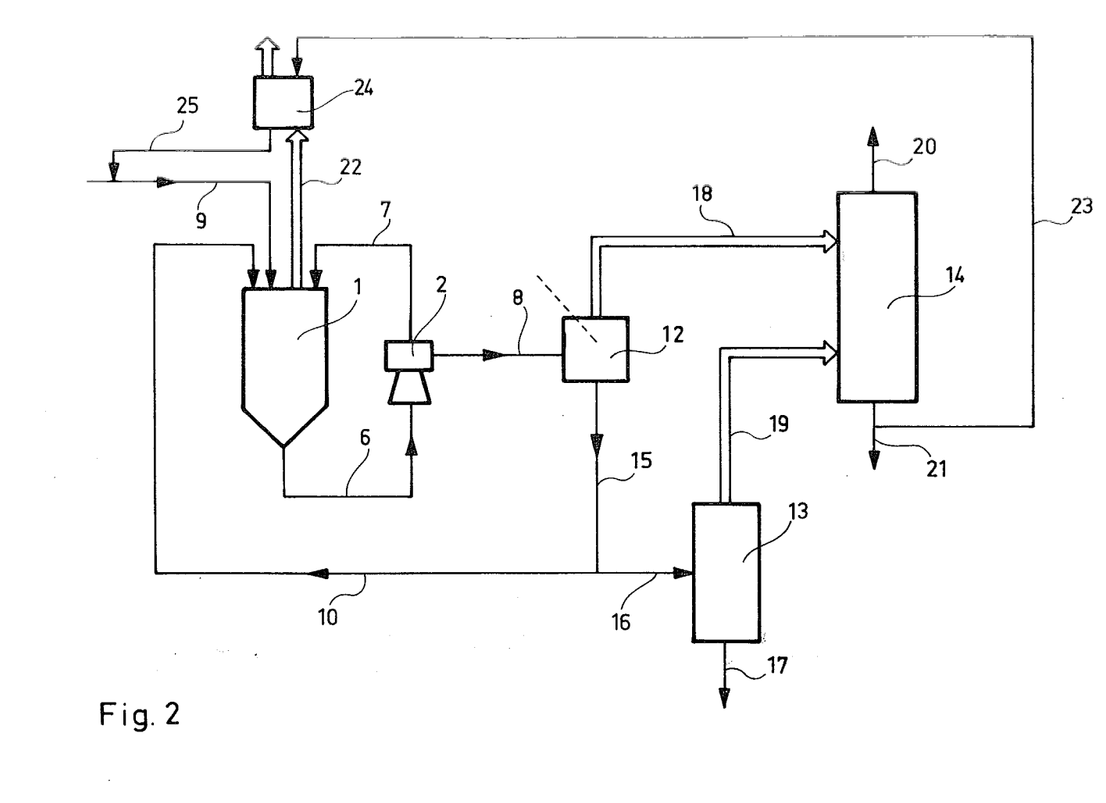
FIG. 2 is a schematic view of a plant for carrying out the method according to the invention.

The plant shown in FIG. 2 comprises a simple evaporator unit 12, a stripping unit 13, and a distillation unit 14. As is obvious, the plant also comprises one fermentor 1 and one centrifugal separator 2, coupled by lines in the same way as in FIG. 1. These units are the same also in FIGS. 3–5. A first liquid bottom flow from evaporator unit 12 is discharged through a line 15, and most of it is recirculated to fermentor 1 through line 10, while a minor part is fed to stripping unit 13 via a line 16 and while a second liquid bottom flow, exhausted of ethanol, is discharged through a line 17. A first vapor flow enriched in ethanol from evaporator unit 12 is conveyed via a line 18, and a second vapor flow enriched in ethanol from stripping unit 13 is conveyed via a line 19 to the distilling unit 14. The feed point of lines 18 and 19 to distilling unit 14 is indicated only schematically. From this distilling unit a concentrated ethanol flow is discharged through a line 20, and a bottom flow, consisting mainly of water more or less completely freed from ethanol, is discharged through a line 21. This bottom flow can be used for washing any adhering ethanol from the $CO_2$-flow discharged from the fermentation. This is shown in FIG. 2, where the bottom flow is fed via a line 23 to a scrubber column 24, to which the $CO_2$-flow from the fermentation is fed via line 22. The scrubber flow thus obtained can be fed through line 25 for diluting the substrate flow delivered through line 9. As shown, the evaporator unit 12 consists of a short column corresponding to one or a few distilling stages, and stripping unit 13 consists of a stripping column provided with a somewhat larger number of distilling stages, for instance clock trays.

Figure 3:
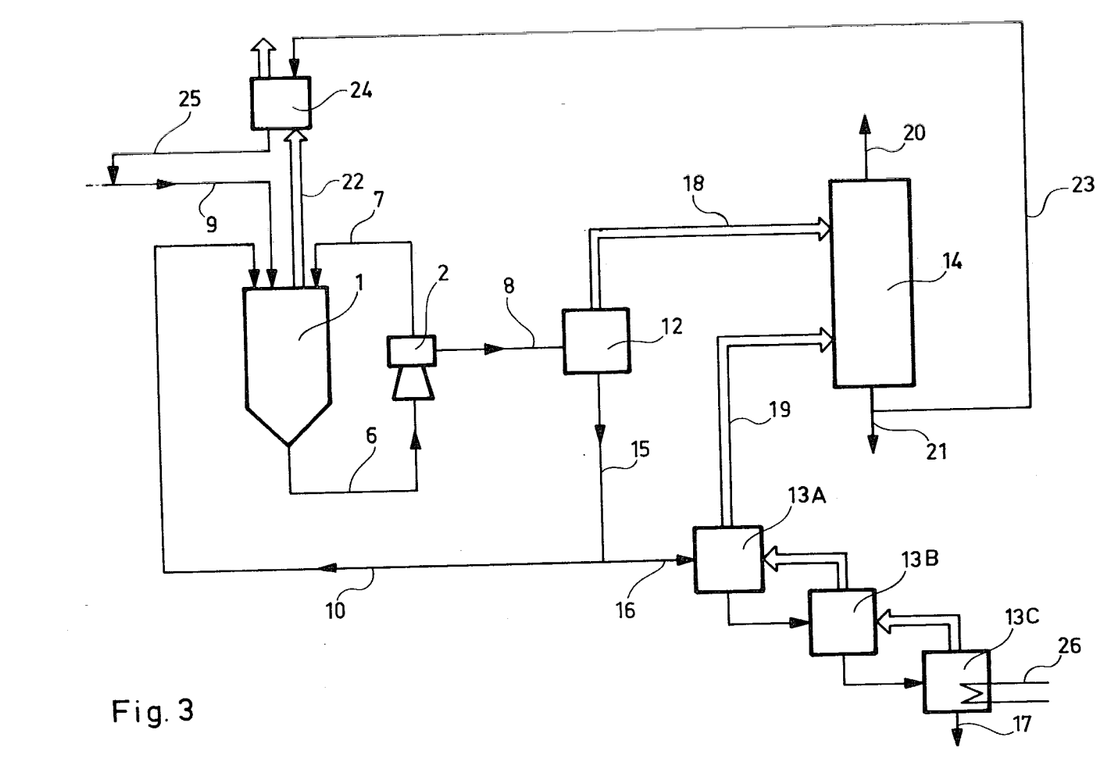
FIG. 3 is a view similar to FIG. 2 but in which the stripping unit comprises three evaporator units coupled in series.

The plant shown in FIG. 3 is similar to that in FIG. 2 with the exception that stripping unit 13 in FIG. 3 consists of three evaporator stages 13A, 13B and 13C, arranged in series in such a way that the bottom flow from evaporator stage 13A is fed to stage 13B, from which the stage 13A received a vapor flow. Similarly, stage 13C received a bottom flow from stage 13B, to which is fed a vapor flow from stage 13C. A slop flow from stage 13C leaves the plant through a line 17. Evaporator stage 13C is assumed to be provided with a heat exchanger in the form of a bottom heater 26 for indirect feed of the energy needed for the stripping. In a plant of the type shown in FIG. 3, which can be used to particular advantage if there are severe deposit problems, these deposits occur primarily in the evaporator unit 12 and secondly in the evaporator stage 13C.

Figure 4:
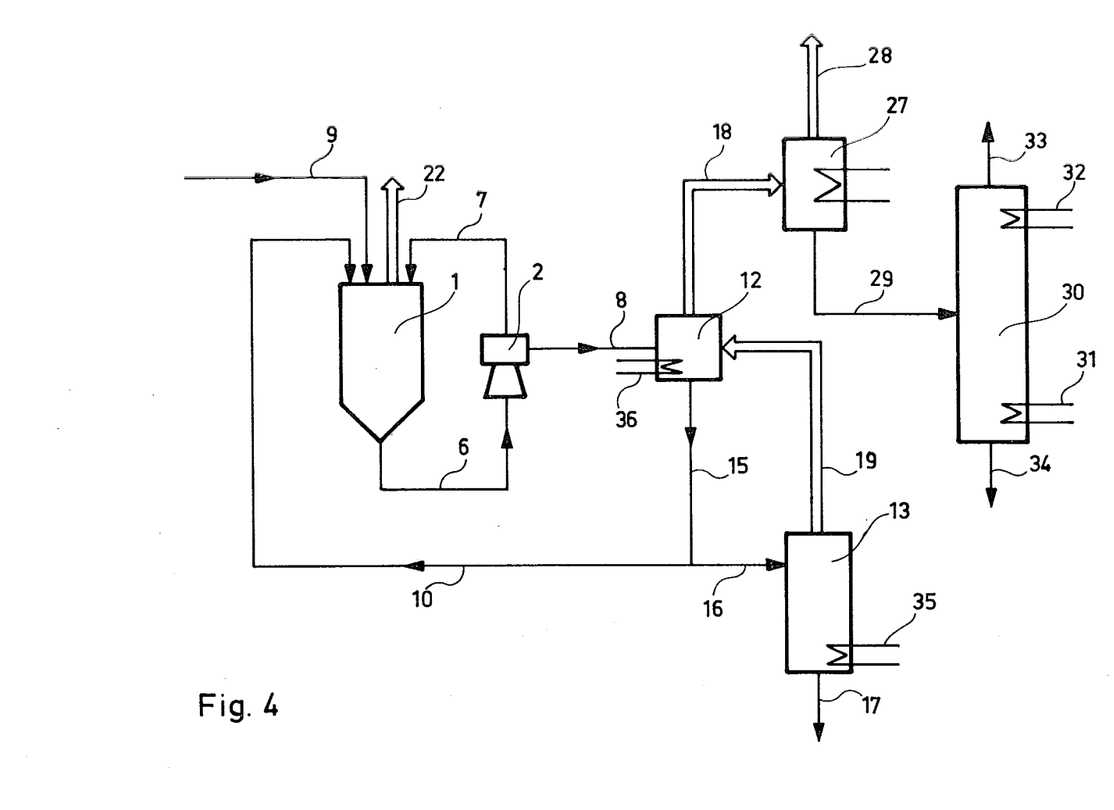
FIG. 4 is a schematic view of a plant for carrying out the new method and comprising a stripping column and a plant for production of ethanol.

In FIG. 4, as in FIGS. 2 and 3, the evaporator unit 12 consists of a short column corresponding to one or a few distilling stages, and the stripping unit 13 consists of a stripping column with a somewhat larger number of distilling stages. The second vapor flow, enriched in ethanol, is fed through line 19 to evaporator unit 12, from which a first vapor flow enriched in ethanol is conveyed through line 18 to a partial condenser 27 consisting of one or a number of condenser stages, from the top of which there is discharged a minor flow of volatile impurities through a line 28, and from the bottom of which there is discharged a flow through line 29 to a combined rectifying and stripping column 30 provided with a bottom heater 31 and a top cooler 32. From this column 30, an ethanol flow through line 33 is obtained with a high content of ethanol, while a bottom flow with a low content of ethanol is discharged through a line 34. The energy for the separation in stripping unit 13 and in evaporator unit 12 can be fed exclusively through a bottom heater 35 in stripping unit 13, but extra energy can also be fed in a bottom heater 36 in evaporator unit 12. It is also possible to feed extra energy in the form of live steam in evaporator unit 12.

The partial condenser 27 can also be replaced by a total condenser, from which the total flow is fed to column 30.

Figure 5:
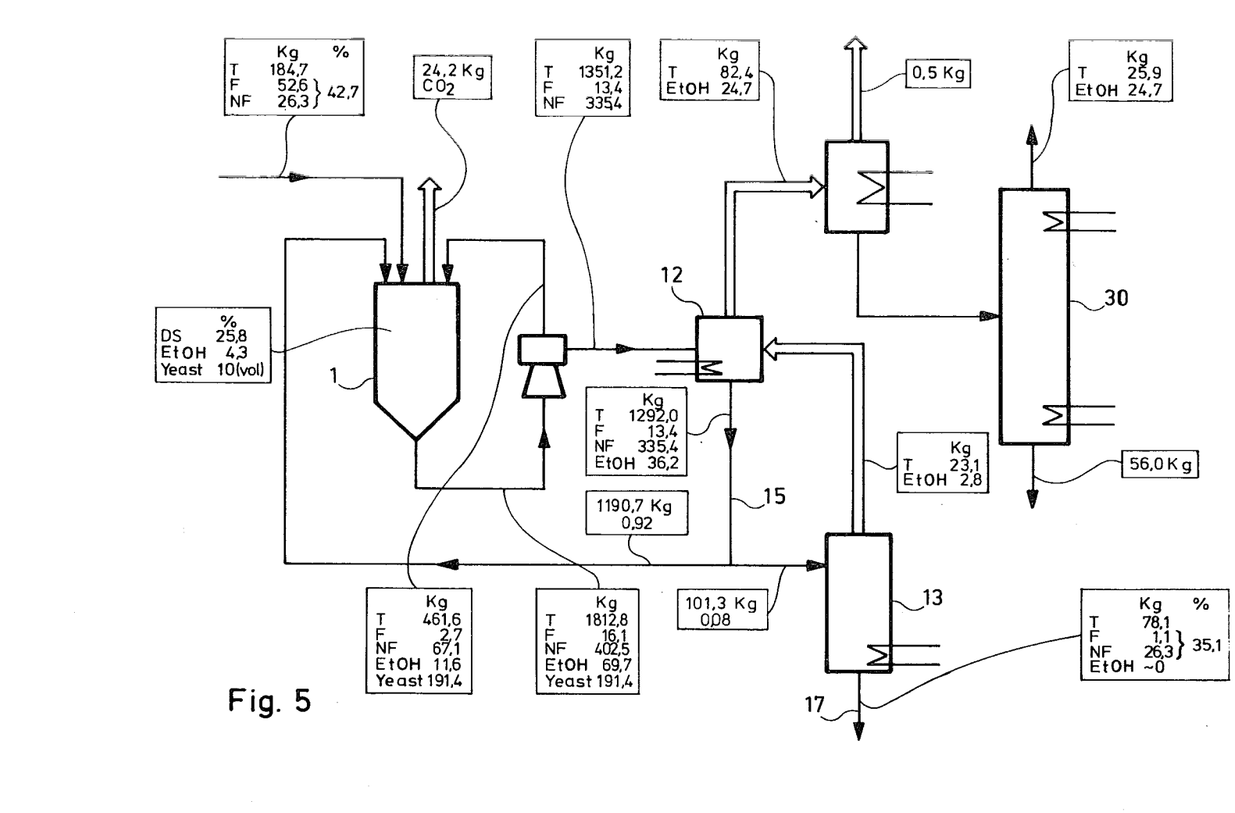
FIG. 5 is a schematic view showing a material balance for a mode of operating the new method.

In FIG. 5 disclosing an example of a material balance, T means total flow in kgs, F means fermentable material and NF means solid dissolved non-fermentable material, primarily salts, etc. Glycerine and other organic impurities have not been accounted for separately. DS means the sum of F+NF, i.e., "dry solids". As is obvious, the DS of the raw material fed is 42.7% (weight) including added water, the DS in the fermentor 1 is 25.8% (weight) (the yeast has not been accounted for) and in the yeast-free flow fed to the simple evaporator unit 12. In the first liquid bottom flow 15 from the evaporator unit 12 the DS is 27.0% (weight), and it is 35.1% (weight) in the slop discharged at 17 from the plant. 92% of the first bottom flow 15 is recirculated to the fermentor, containing 2.8% (weight) ethanol. This means that there is a relatively high concentration of ethanol in the recirculated flow. The energy for separation in the evaporator unit 12 and in the stripping unit 13 is fed partly as indirect steam in the stripping unit and partly as indirect or live external steam in the evaporator unit.

Figure 6:
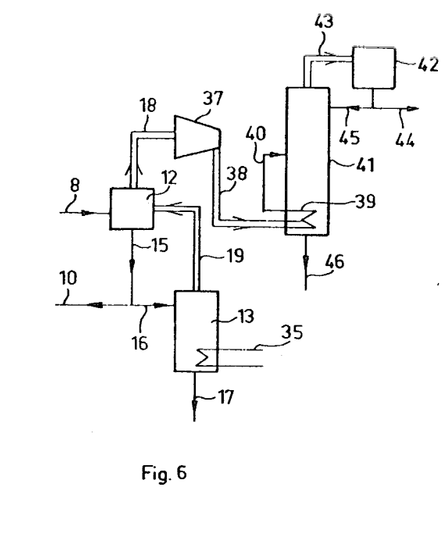
FIG. 6 is a schematic view of a plant generally similar to that in FIG. 4 but including a thermo compressor for compressing vapors fed to the rectifying column.
Figure 7:
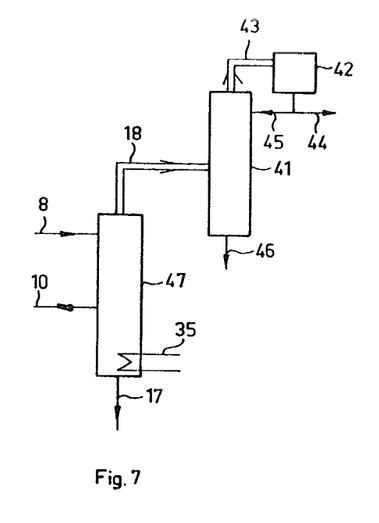
FIG. 7 is a schematic view generally similar to FIG. 4 but in which the simple evaporator unit is combined with the stripping unit to one column unit.
Figure 8:
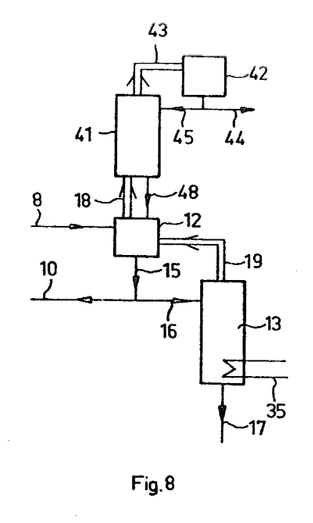
FIG. 8 is a schematic view generally similar to FIG. 4 but in which a liquid flow is recirculated from the rectifying column to the evaporator unit.

FIGS. 6-8 show a few further modifications of the embodiment shown in FIG. 4, in which the vapors from the stripping unit are fed to the simple evaporator unit as direct heating medium. Symbols 8-35 from FIG. 4 are also used in FIGS. 6-8 for the corresponding units and lines. The vapors passing through line 18 from the evaporator unit 12 are sent to the rectifying column 41 provided with a top condensor 42 for condensing vapors from line 43 rich in ethanol, the condensate passing to a liquid discharge flow 44 and a liquid reflux flow 45. In FIG. 6 and FIG. 7 a liquid bottom flow 46 poor in ethanol is discharged from the rectifying column 41.

In the modification shown in FIG. 6, the vapors from the evaporator unit 12 are compressed in a thermo compressor 37 to form an ethalpy enriched vapor flowing through line 38. This vapor is fed to a reboiler-condensor unit 39 and is condensed to a liquid flow 40 which is fed to the rectifying column 41.

The modification shown in FIG. 7 consists of combining the evaporator unit 12 and the stripping unit 13 of FIG. 4 in one column 47, the stripping unit 13 corresponding to part of column 47 below line 10 for recirculation of liquid to the fermentor, and the evaporator unit 12 corresponding to part of column 47 above said line 10.

In the modification according to FIG. 8, the vapor flow through line 18 from the evaporator unit 12 is fed to the lowest distilling stage in the rectifying column 41 and a liquid bottom flow 48 from the rectifying column 41 is recirculated to the evaporator unit 12.

Even higher DS-content can be operated in the fermentor. The ability of the yeast to stand osmotic pressure probably sets a limit. DS-contents of 25-30% (weight) are possible.

The process can be controlled in different ways. Thus the ethanol concentration of the first vapor flow, enriched in ethanol, can be controlled by varying the energy feed to the simple evaporator unit or to the stripping unit. The level in the fermentor can be controlled by varying the portion of the first liquid bottom flow recirculated to the fermentor.

We claim:

1. In the production of ethanol from a substrate containing carbohydrate, the method which comprises the continuous steps of delivering the substrate to a fermentor to provide a fermenting liquor, feeding a flow of said liquor from the fermentor to a separating unit and there separating the liquor into a yeast concentrate flow and a yeast-free flow, recirculating said yeast concentrate flow to the fermentor, feeding said yeast-free flow to a simple evaporator unit and there separating it into a first ethanol-enriched vapor flow and a first liquid bottom flow, treating said first vapor flow to produce ethanol of a desired quality, recirculating a major part of said first liquid bottom flow to the fermentor, feeding a minor residual part of said first liquid bottom flow to a stripping unit, and separating said residual part in the stripping unit into a second ethanol-enriched vapor flow and a second liquid bottom flow exhausted of ethanol.

2. The method of claim 1, comprising also feeding at least a major part of said second ethanol-enriched vapor flow to said evaporator unit.

3. The method of claim 1, comprising also combining at least part of said second ethanol-enriched vapor flow with said first ethanol-enriched vapor flow.

4. The method of claim 1, in which said first vapor flow is treated in a rectifying column to produce said ethanol of a desired quality, the method comprising also feeding at least part of said second vapor flow to said rectifying column as a heating medium.

5. The method of claim 1, in which said first vapor flow is treated in a rectifying column to produce said ethanol of a desired quality, the method comprising also feeding at least part of at least one of said first and second vapor flows to a thermo compressor, and heating said rectifying column by said thermo compressor.

6. The method of claim 1, in which said treating of said first vapor flow includes feeding at least part of it to the lowest distilling stage in a rectifying column, the method comprising also recirculating a liquid flow from said lowest stage to the evaporator unit.

7. The method of claim 1, in which the energy for the separation in said evaporator unit is supplied at least partly in the form of external live steam.

8. The method of claim 1, in which at least part of the energy for the separation in said evaporator unit is supplied indirectly by heat exchange.

9. The method of claim 8, in which external steam is used for said heat exchange.

10. The method of claim 1, in which said stripping unit includes a plurality of evaporator stages coupled in series, the vapor flow from one evaporator stage being fed to the previous stage while the bottom flow from said previous stage is fed to said one stage.

11. The method of claim 1, in which at least one of said separations is performed at substantially atmospheric pressure.

12. The method of claim 1, in which at least one of said separations is performed at subatmospheric pressure.

13. The method of claim 1, in which said simple evaporator unit and said stripping unit are combined in a single column, said yeast-free flow being fed to the upper portion of the column where the evaporator unit is located, said first liquid bottom flow being discharged from the column at a level located at the lower portion of the evaporator unit and being divided to form said major part and said minor residual part, said minor residual part of said first bottom flow being fed to the lower portion of said column where said stripping unit is located, said second ethanol-enriched vapor flow passing upwardly in said lower portion of the column and leaving the stripping unit at about said level.

14. The method of claim 13, in which said second ethanol-enriched vapor flow is passed directly through said level and into the evaporator unit.

* * * * *